United States Patent [19]
Rosenberg

[11] Patent Number: 5,824,056
[45] Date of Patent: Oct. 20, 1998

[54] IMPLANTABLE MEDICAL DEVICE FORMED FROM A REFRACTORY METAL HAVING A THIN COATING DISPOSED THEREON

[75] Inventor: Duane L. Rosenberg, Columbia Heights, Minn.

[73] Assignee: Medtronic, Inc., Minneapolis, Minn.

[21] Appl. No.: 834,779

[22] Filed: Apr. 3, 1997

Related U.S. Application Data

[60] Division of Ser. No. 568,028, Dec. 6, 1995, Pat. No. 5,765,418, which is a continuation-in-part of Ser. No. 243,348, May 16, 1994, abandoned.

[51] Int. Cl.⁶ ........................................................ A61F 2/06
[52] U.S. Cl. .............................. 623/1; 606/191; 607/121; 607/36; 427/2.24
[58] Field of Search ........................... 623/1, 12; 606/191, 606/195, 198; 427/2.24; 607/1, 2, 36, 121

[56] References Cited

U.S. PATENT DOCUMENTS

| | | |
|---|---|---|
| 3,339,271 | 9/1967 | Durfee et al. . |
| 3,429,158 | 2/1969 | McDonald et al. . |
| 3,641,795 | 2/1972 | Lester et al. . |
| 3,698,050 | 10/1972 | Rubin . |
| 3,905,828 | 9/1975 | Barber . |
| 4,081,335 | 3/1978 | Von Stutterheim et al. . |
| 4,514,589 | 4/1985 | Aldinger et al. . |
| 4,815,309 | 3/1989 | Sawarda et al. . |
| 4,859,811 | 8/1989 | Sawada et al. . |
| 5,230,337 | 7/1993 | Dohl et al. .................................. 607/5 |
| 5,271,417 | 12/1993 | Swanson et al. ....................... 607/122 |
| 5,725,572 | 3/1998 | Lam et al. .................................. 623/1 |

FOREIGN PATENT DOCUMENTS

| | | |
|---|---|---|
| 207467 | 6/1956 | Australia . |
| 38-7461 | 5/1963 | Japan . |
| 237912 | 2/1990 | Japan . |
| 259109 | 2/1990 | Japan . |

*Primary Examiner*—Paul B. Prebilic
*Attorney, Agent, or Firm*—Thomas F. Woods; Harold R. Patton

[57] ABSTRACT

An implantable medical device formed from a drawn refractory metal and having an improved biocompatible surface is described. The method by which the device is made includes coating a refractory metal article with platinum by a physical vapor deposition process and subjecting the coating article to drawing in a diamond die. The drawn article can be incorporated into an implantable medical device without removing the deposited metal.

1 Claim, 2 Drawing Sheets

IMPLANTABLE MEDICAL DEVICE FORMED FROM A REFRACTORY METAL HAVING A THIN COATING DISPOSED THEREON

This application is a divisional of application Ser. No. 08/568,028 filed Dec. 6, 1995 now U.S. Pat. No. 5,765,418 which is a continuation-in-part of Ser. No. 08/243,348 filed May 16, 1994 now abandoned.

BACKGROUND OF THE INVENTION

This invention relates to implantable medical devices and in particular to implantable medical devices which include biocompatible refractory metals which are drawn into elongated shapes.

Medical devices often include biocompatible refractory metals such as titanium or tantalum which may come into contact with body fluids as the device is implanted in a human or animal body. For example, titanium may be used in surgical staples and in electrical leads. Tantalum may be used in stents, catheters and other intravascular devices. These materials are preferred for such applications because they are biocompatible and corrosion resistant, that is, that they will resist the corrosive influences of long term implantation in body fluids and will not provoke adverse reactions by the host body when implanted in contact with body tissue or body fluids such as blood. It will be appreciated by those skilled in the art that in such devices, it is desirable to have a uniform, smooth surface finish which is free of foreign material which may provoke an adverse response from the body or which may accelerate corrosive deterioration of the implanted device.

Most wire, bar and tubing is drawn (hot or cold) by means of dies with diamond or tungsten carbide inserts. Diamond dies are in a class by themselves for resisting wear and producing the best surface on a drawn article. When an article, such as wire, is to be drawn to smaller cross-sections, it is typical to coat it with various materials known as drawing compounds.

It would be desirable in the case of titanium and tantalum drawpieces to use a diamond die so as to obtain the best surface for articles to be used as in conjunction with implantable medical devices such as staples, wire mesh electrodes and patches, catheters guide wires, and sutures. However, titanium and tantalum can react with diamond (carbon) dies and are therefore incompatible.

Presently, the practice is to coat the titanium, tantalum or other diamond-incompatible material with various materials, draw it in the diamond die and then chemically etch the coating away. Unfortunately, this leaves a relatively rough surface of poor quality.

It is therefore an object of the present invention to provide a method for making an implantable medical device without requiring the drawn refractory material to be etched after drawing.

SUMMARY OF THE INVENTION

It has been discovered that titanium and tantalum drawings which have been coated with a biologically inert lubricant metal, especially wire or ribbon drawpieces have a smoother and more uniform surface than drawpieces produced as in the prior art described above when such a coated drawpiece is drawn in a diamond die. This method is also lower in cost than the prior method when yield and quality are considered. The coating of biologically inert lubricant metal (e.g. platinum or gold) is not removed for ultimate use of an article treated according to this invention. For example, platinum is intimately bonded to titanium by the annealing process as part of the diamond drawing procedure. Anneal temperatures, reduction area, feed rates, etc., need to be optimized in each given situation for bonding of coating and minimizing formation of intermetallics, depending on wire size, annealing temperature, etc.

In particular, the method for making a medical device according to the present invention comprises the steps of providing an elongated article of a biocompatible refractory metal, coating the refractory metal article with a biologically inert lubricant metal such as platinum by a physical vapor deposition process to a coating thickness of up to about 3000 Å subjecting the article to drawing in a diamond die and incorporating the drawn article into an implantable medical device at a portion of the medical device intended for exposure to body fluids without removing the deposited metal. The resulting article maintains the corrosion resistance and biocompatibility of the base material without requiring removal of the deposited metal.

DETAILED DESCRIPTION OF THE PREFERRED EMBODIMENTS

While this invention may be embodied in many different forms, there are described in detail herein specific preferred embodiments of the invention. This description is an exemplification of the principles of the invention and is not intended to limit the invention to the particular embodiments illustrated.

Figure 1:
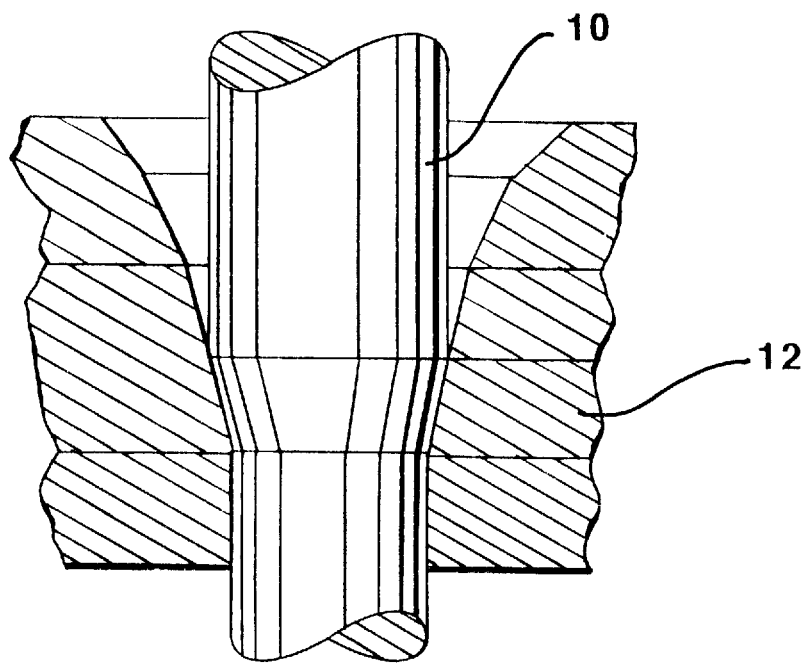
FIG. 1 is a schematic showing of a drawing die.

FIG. 1 is a typical diamond wire drawing die as may be used for reduction of a drawpiece, in this case wire. The die is shown for use with round wire, however it can be of a configuration for use of ribbon-like ire as well. It will typically be of the type including diamond inserts (not shown for simplicity) as is known in the art.

As can be seen in FIG. 1, a refractory metal (e.g. titanium) wire 10 of a relatively large cross-section is reduced on being subjected to drawing within the die 12. In order to avoid interaction between a refractory metal drawpiece article, such as the wire 10, and the diamond (carbon) inserts in die 12, the drawpiece 10 is coated with a layer of a biologically inert lubricant metal (e.g. platinum) 14.

Figure 2:
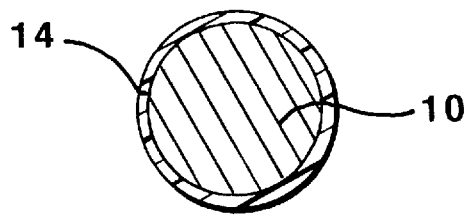
FIGS. 2 and 3 are alternative embodiments of a refractory metal wire with a coating of a biologically inert lubricant metal.
Figure 3:
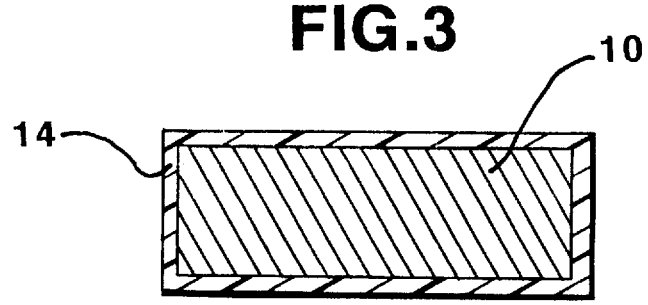

FIG. 2 shows such a round titanium wire 10 in cross-section having a platinum coating 14. FIG. 3 shows a similar coated ribbon-like wire 10 in cross-section with titanium, coating 14.

The refractory metal article may be a pure metal or an alloy (e.g. the titanium alloy Ti64-6Al-4V, which is presently preferred for wire to be used for many medical purposes). Other titanium-based alloys may be used as well.

In order to produce a thin platinum coating, it is preferred that it be provided by a physical vapor or deposition process such as sputtering which is particularly preferred. For example, 500 foot lengths of titanium wire were coated with platinum by sputtering in a roll coater at 900 watts and 5 ft/min wire speed with a resultant thickness of about 2200 Å.

Thickness ranging from about 500 Å to about 3000 Å are generally preferred. These conditions are generally satisfactory for reductions from about 0.025" diameter to about 0.003 diameter.

Multiple spools were coated by two DC magnetron cathodes running at 900 watts each. Higher powers with proportionally higher rates are possible with larger cathodes. The sputtering gas was argon. Krypton gas would work as well. The necessary conditions are known in the art.

For sputtering coils of wire, a roll coater may be conveniently used. A typical roll coater (not shown) consists of a vacuum chamber, sputtering sources and targets, a pumping system and a winding system. The wire spools may be unwound in the vacuum chamber during sputtering. The winding system feeds the wire over various rollers and in front of the sputtering source while maintaining a constant speed and tension until the entire wire lengths are coated.

Sputter coated Ti64-6Al-4V wire was successfully drawn in a diamond die and found to possess a smooth surface with one and multiple die interaction(s).

Figure 4:
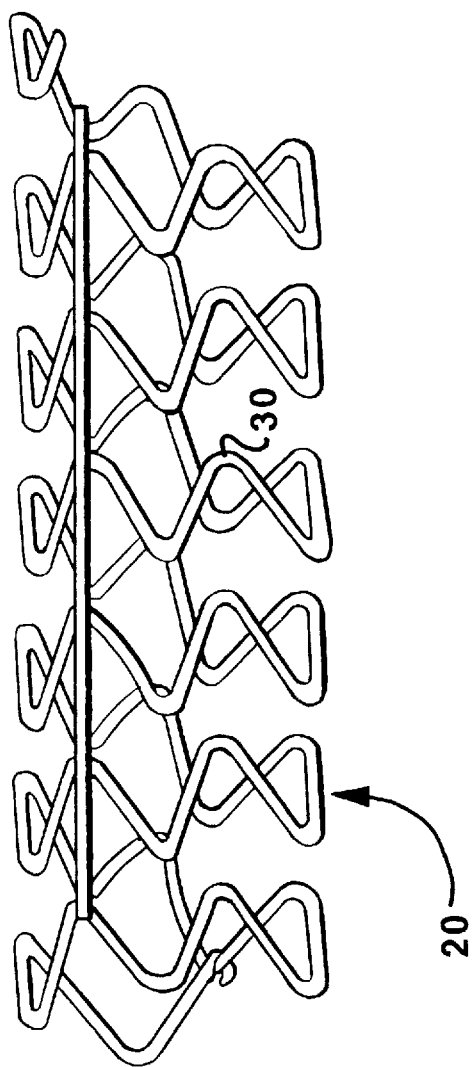
FIG. 4 is a medical device (an intravascular stent) made according to the present invention.

Wire made as described above can be incorporated into medical devices by appropriate manufacturing methods. For example, the intravascular stent 20 shown in FIG. 4 can be made as disclosed in U.S. Pat. Nos. 4,886,062 and 5,133,732 issued to Wiktor which patents are incorporated by reference herein. Either tantalum or titanium wire 30 could be used during its construction depending on the mechanical properties desired in the finished product. The resulting stent 20 may be delivered into the interior of a blood vessel of a living animal or human and permanently implanted there with the tantalum or titanium wire 30 in contact with blood and tissue to support the walls of the blood vessel.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

I claim:

1. An implantable medical device comprising an elongated article intended for exposure to body tissue or body fluids, the elongated article comprising a refractory metal coated by a physical vapor disposition process to form a coating thereon, the coating forming a biologically inert metal lubricant having a thickness ranging between about 500 Angstrom and about 3000 Angstrom, the article being drawn in a diamond die to form a smooth biocompatible surface finish.

* * * * *